(12) United States Patent
Bosch

(10) Patent No.: US 10,059,702 B2
(45) Date of Patent: Aug. 28, 2018

(54) INHIBITORS OF LC3/ATG3 INTERACTION AND THEIR USE IN THE TREATMENT OF CANCER

(71) Applicant: THE JOHNS HOPKINS UNIVERSITY, Baltimore, MD (US)

(72) Inventor: Jurgen Bosch, Pikesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/847,593

(22) Filed: Sep. 8, 2015

(65) Prior Publication Data

US 2016/0176860 A1 Jun. 23, 2016

Related U.S. Application Data

(60) Provisional application No. 62/047,271, filed on Sep. 8, 2014.

(51) Int. Cl.
*C07D 417/12* (2006.01)
*C07D 417/14* (2006.01)
*C07D 417/04* (2006.01)
*A61K 45/06* (2006.01)

(52) U.S. Cl.
CPC ............ *C07D 417/12* (2013.01); *A61K 45/06* (2013.01); *C07D 417/04* (2013.01); *C07D 417/14* (2013.01)

(58) Field of Classification Search
CPC .. C07D 417/12; C07D 417/04; C07D 417/14; A61K 45/06
USPC ........................................................ 514/333
See application file for complete search history.

(56) References Cited

U.S. PATENT DOCUMENTS 4,450,150 A 5/1984 Sidman
6,586,423 B2 * 7/2003 Bilodeau .............. C07D 417/14
514/217.04

OTHER PUBLICATIONS

Bilodeau et al Bioorg. Med. Chem. Lett, 2004, 14, 2941-2945.*
Taurins et al Journal of Heterocyclic Chemistry, 1970, 7(5), 1137-1141; STN abstract.*
Gavezzotti Acc. Chem. Res. 1994, 27, 309-314.*
Hain A.U.P., et al., Structural characterization and inhibition of the Plasmodium Atg8-Atg3 interaction. J Struct Biol, 2012. 180: p. 551-562.
Hain, A.U.P., et al., Identification of an Atg8-Atg3 protein-protein interaction inhibitor from the Medicines for Malaria Venture Malaria Box active in blood and liver stage P. falciparum parasites. J Med Chem. Jun. 12, 2014;57 (11):4521-31. doi: 10.1021/jm401675a. Epub May 19, 2014.
Peppard, J.V., et al., Identifying Small Molecules which Inhibit Autophagy: a Phenotypic Screen Using Image-Based High-Content Cell Analysis., in Curr Chem Genomics Transl Med2014. p. 3-15.

* cited by examiner

*Primary Examiner* — Yevgeny Valenrod
(74) *Attorney, Agent, or Firm* — John Hopkins Technology Ventures

(57) ABSTRACT

The present inventors discovered that the molecule pyridinylthiazolamine (PTA) specifically prevents the protein-protein interaction of hLC3 with hAtg3 in vitro and in cell based assays. The inventors have developed a novel class of PTA analogs which also prevents the protein-protein interaction of hLC3 with hAtg3 in vitro, and in cell based assays, and which can be used in prior to, or in combination with chemotherapeutic agents to treat proliferative diseases such as cancer.

11 Claims, 5 Drawing Sheets

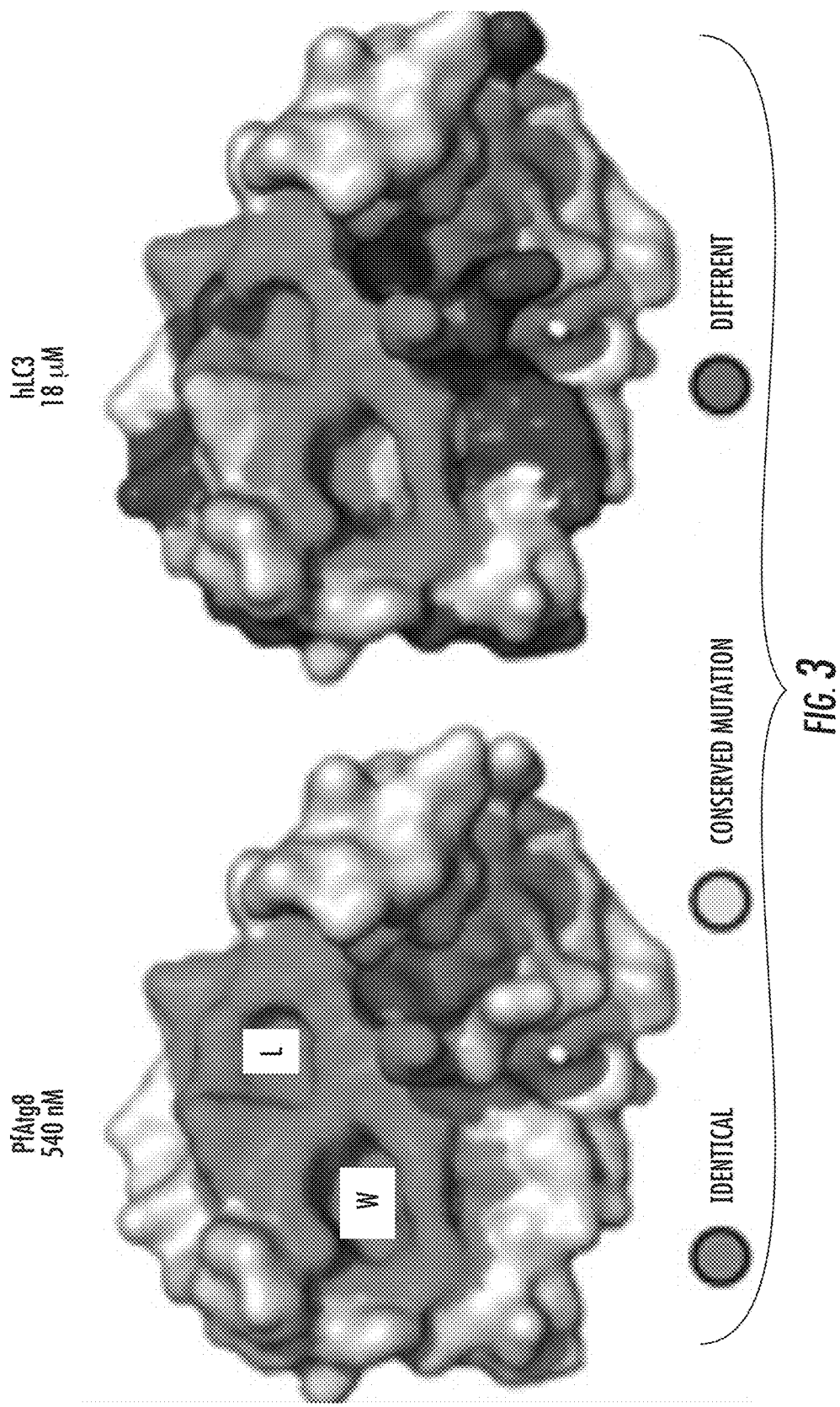

INHIBITORS OF LC3/ATG3 INTERACTION AND THEIR USE IN THE TREATMENT OF CANCER

REFERENCE TO RELATED APPLICATIONS

This application claims the benefit of Provisional U.S. Patent Application No. 62/047,271, filed Sep. 8, 2014, and is hereby incorporated by reference for all purposes as if fully set forth herein.

BACKGROUND OF THE INVENTION

Autophagy is a catabolic process performed by eukaryotic cells in order to maintain homeostasis and to degrade unwanted or toxic cellular content such as misfolded proteins. The classical autophagy pathway in mammals is depicted in FIG. 1A. Observations indicate a critical role of autophagy in cancer cells e.g. survival of colorectal tumors is abolished when treated with autophagy inhibitors. However, the exact role of autophagy in cancer is very complex and highly debated. On the one hand, autophagy has been associated with increased survival of tumors, for example, under hypoxic or nutrient deprivation conditions; on the other hand, autophagy prevents DNA damage in normal cells, and therefore can serve a tumor suppressing role within the cell.

Many autophagy inhibitors such as 3-methyladenine (3-MA) or hydroxychloroquine (CQ) are promiscuous compounds. Moreover, many FDA-approved drugs interact with multiple protein targets Inhibition of mTOR through rapamycin leads to an activation of autophagy, while inhibition of VPS34 by Wortmannin prevents autophagy (FIG. 1A). In addition, the protein targets mTOR or Beclin1 are effectors of multiple pathways and are therefore pleiotropic by nature.

Current intervention methods targeting the autophagy pathway are somewhat indirect and intervene very early in the pathway, which may allow the cell to regulate the autophagy pathway through other checkpoint events. Recently, a research group at Sanofi recognized the lack of direct autophagy inhibitors and its negative impact on the cancer field. They utilized an assay comprising a fusion construct expressing enhanced green fluorescent protein (EGFP)-LC3 in two tumor cell lines and monitored the granular fluorescence in the presence of small molecules. Hence, they were able to directly measure the effect of the small molecules on the lipidation state of EGFP-LC3, using loss of granulosity as an indicator of the unlipidated form. This assay was followed with a second assay which looked specifically at the induction of cell death under starvation conditions in the presence of the small molecules identified in the primary screen. Both can be used to screen novel compounds for inhibition of LC3/Atg3 interaction.

As such, there still exists an unmet need for novel compounds which can act as direct autophagy inhibitors and their use in the study and treatment of cancer.

SUMMARY OF THE INVENTION

The present inventors discovered that PTA specifically prevents the protein-protein interaction of hLC3 with hAtg3 in vitro. The inventors have created a novel class of PTA analogs which also prevents the protein-protein interaction of hLC3 with hAtg3 in cell cultures, and which can be used to treat proliferative diseases such as cancer.

In accordance with an embodiment, the present invention provides a compound of formula I:

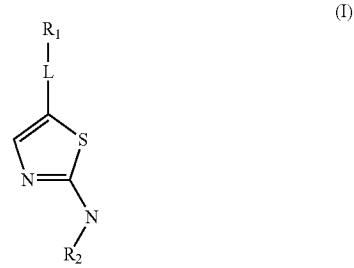

or salt solvate, or stereoisomer thereof, wherein $R_1$ is an aryl, pyrimidyl, napthalenyl or heteronapthalenyl group which may be substituted with one or more $C_1$-$C_6$ alkyl or substituted $C_1$-$C_6$ alkyl groups; wherein L is a linker group of 0 or 1, comprising an alkylamino group; wherein $R_2$ is aryl or pyrimidyl group which may be substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsulfonyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, or a halogen, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; and optionally wherein $R_2$ is linked to the aminothiazole ring of formula I by an amide linkage.

In accordance with an embodiment, the present invention provides compounds of formula II:

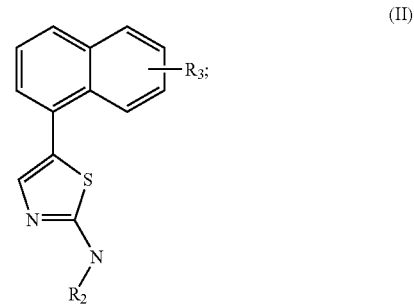

wherein $R_2$ is aryl or pyrimidyl group which may be substituted at $C_2$-$C_4$ with one or more $C_1$-$C_6$ alkyl groups or a halogen, and $R_3$ is one or more $C_1$-$C_6$ alkyl or substituted $C_1$-$C_6$ alkyl groups.

In accordance with an embodiment, the present invention provides a compound of formula III:

(III)

wherein R$_2$ is aryl or pyrimidyl group which may be substituted at C$_2$-C$_4$ with one or more C$_1$-C$_6$ alkyl groups or a halogen, and R$_3$ is one or more C$_1$-C$_6$ alkyl or substituted C$_1$-C$_6$ alkyl groups.

In accordance with an embodiment, the present invention provides a compound of formula IV:

(IV)

wherein R$_2$ is aryl or pyrimidyl group which may be substituted at C$_2$-C$_4$ with one or more C$_1$-C$_6$ alkyl groups or a halogen, and R$_3$ is one or more C$_1$-C$_6$ alkyl or substituted C$_1$-C$_6$ alkyl groups.

In accordance with another embodiment, the present invention provides compounds of formula I, wherein the compound is selected from the group consisting of:

(1)

(2)

(3)

(4)

(5)

-continued (6)
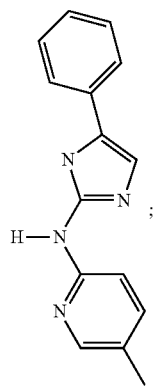

(7)
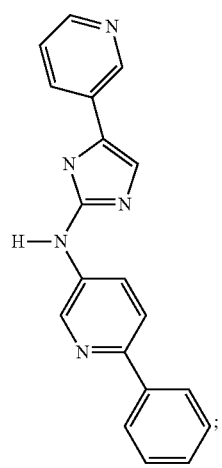

(8)
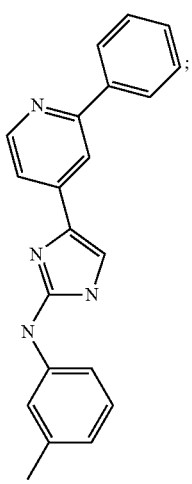

-continued (9)
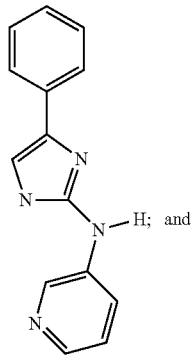
H; and

(10)
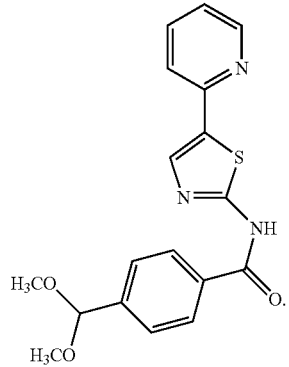

In accordance with a further embodiment, the present invention provides a pharmaceutical composition comprising one or more compounds of formula I, as described above, or a salt, solvate or stereoisomer thereof, and a pharmaceutically acceptable carrier.

In accordance with another embodiment, the present invention provides a pharmaceutical composition one or more compounds of formula I, as described above, or a salt, solvate or stereoisomer thereof, and a pharmaceutically acceptable carrier and further comprises at least one chemotherapeutic agent.

In accordance with another embodiment, the present invention provides a pharmaceutical composition as described above, for use in a medicament, preferably for use in a medicament for the treatment of cancer or a proliferative disease in a subject comprising administering to the subject an effective amount of the medicament.

In accordance with another embodiment, the present invention provides a method for treating cancer in a subject comprising administering to the subject an effective amount of a compound of formula I, or a salt solvate, or stereoisomer thereof.

In accordance with a further embodiment, the present invention provides a method for treating cancer in a subject comprising administering to the subject an effective amount of a pharmaceutical composition comprising a compound of formula I, or a salt solvate, or stereoisomer thereof, and a pharmaceutically effective carrier.

In accordance with yet another embodiment, the present invention provides a method for treating cancer in a subject comprising administering to the subject an effective amount of a pharmaceutical composition comprising a compound of formula I, or a salt solvate, or stereoisomer thereof, at least one chemotherapeutic agent, and a pharmaceutically effective carrier.

BRIEF DESCRIPTION OF THE DRAWINGS

FIG. 3 shows the conservation of the W-/L-site and their respective binding affinity to PTA. To maintain the identical view, residue differences were painted onto the PfAtg8 structure. Residues in the proximity of the W-/L-site of hLC3 lead to lower binding affinities of our current molecule targeting the Atg8-Atg3 interaction.

DETAILED DESCRIPTION OF THE INVENTION

Figure 1A:
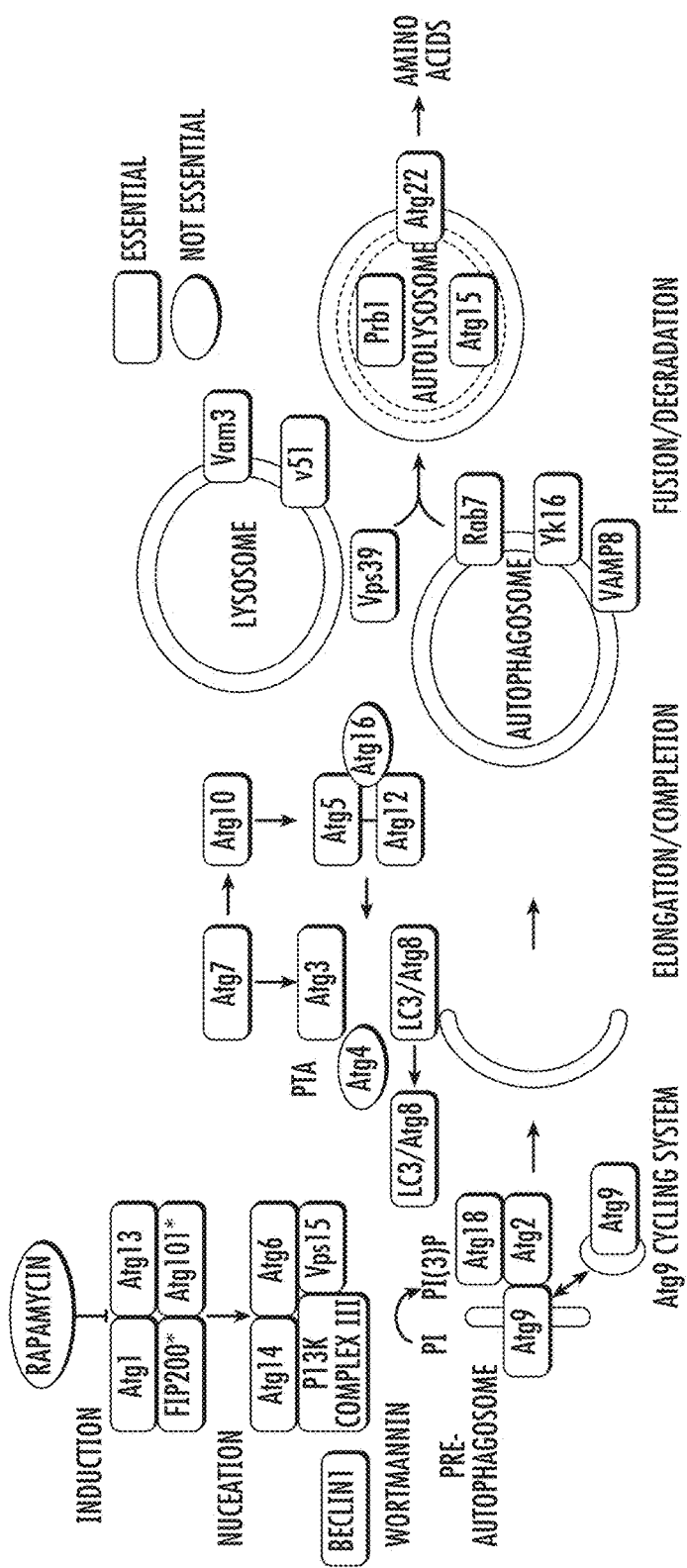
FIGS. 1A-1B are an overview of the mammalian autophagy pathway. 1A) Proteins essential for autophagy are depicted as rectangles. Ovals represent proteins whose essentiality is not known. Indicated in red are two known inhibitors used in cancer treatment. Purple signifies the interaction targeted by our PTA molecule. Figure adapted from Hain et al. 2013. 1B) Schematic of the proteins involved in the LC3/Atg8 PE-conjugation pathway.
Figure 1B:
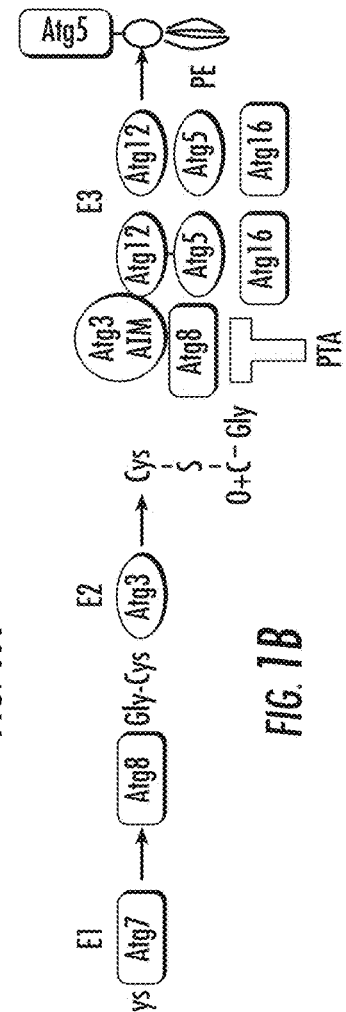

The present inventors recently identified anti-malarial compounds with a Pyridinylthiazolamine (PTA) scaffold inhibit the critical phosphatidylethanolamine (PE)-conjugation step of LC3/Atg8 (FIG. 1) (J. Med. Chem. 2014, 57, 4521-4531 (2014)), included in U.S. Patent Application No. 61/984,315, and incorporated by reference herein. The inventors' PTA compounds were designed to interfere with the Atg8-Atg3 protein-protein interaction and thereby prevent the lipidation of Atg8 (hLC3-II). Only the PE-conjugated form (hLC3-II) participates in elongation of the autophagosomal membrane, preparing the encapsulated material for fusion with the lysosome for nutrient recycling and degradation processes. Before conjugation to PE, most LC3/Atg8 orthologues require proteolytic processing of one or several amino acids by Atg4 to expose a C-terminal glycine (FIG. 1B). The exposed C-terminus of Atg8 is then attached to its E1 activating enzyme, Atg7, through a thioester bond that requires activation by ATP hydrolysis. Atg8 is then transferred to its E2 conjugating enzyme, Atg3, to form another thioester bond before being transferred to PE in the incipient phagophore membrane. This complex activation cascade yielding LC3-II can be regulated at any of the above steps. Therefore inhibiting the very last step in this conjugation process can be a very effective approach, as no feedback to the prior activation steps is possible.

In accordance with an embodiment, the present invention provides a compound of formula I:

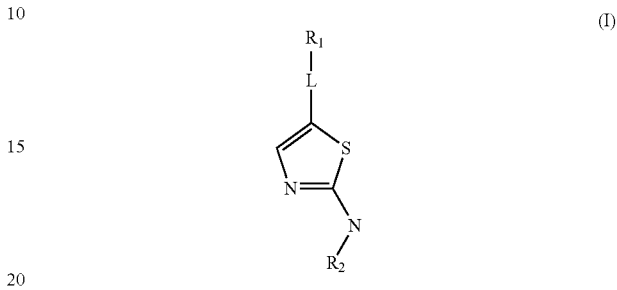

or salt solvate, or stereoisomer thereof, wherein $R_1$ is an aryl, pyrimidyl, napthalenyl or heteronapthalenyl group which may be substituted with one or more $C_1$-$C_6$ alkyl or substituted $C_1$-$C_6$ alkyl groups; wherein L is a linker group of 0 or 1, comprising an alkylamino group; wherein $R_2$ is an aryl pyridyl or pyrimidyl group which may be substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsulfonyl $C_1$-$C_6$ alkyl, hydroxy $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, or a halogen, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl and optionally wherein $R_2$ is linked to the aminothiazole ring of formula I by an amide linkage.

In the compounds disclosed herein, including, e.g., General Formula I, the "hydrocarbon group" of the "hydrocarbon group which may be substituted" represented by $R_1$ may be exemplified by a straight-chained or cyclic hydrocarbon group (e.g., an alkyl group, an alkenyl group, an alkynyl group, a cycloalkyl group, an aryl group, an arylalkyl group, alkylol group, hydroxyalkyl group, alkoxy group, alkoxyalkyl group, a branched or straight-chain alkylamino, dialkylamino, or alkyl or dialkylaminoalkyl, or thioalkyl, thioalkenyl, thioalkynyl, aryloxy, thioaryl, thioheteroaryl, acyloxy, thioacyl, amido, sulphonamido, etc.), or the like. Among these, straight-chained or cyclic hydrocarbon groups having 1 to 16 carbon atoms are preferred.

Examples of the "cycloalkyl group" preferably include a $C_{3-8}$ cycloalkyl group (e.g., a cyclopropyl group, a cyclobutyl group, a cyclopentyl group, a cyclohexyl group, etc.) and the like.

Examples of the "aryl group" preferably include a $C_{6-14}$ aryl group (e.g., a phenyl group, a 1-naphthyl group, a 2-naphthyl group and the like.

Examples of the "arylalkyl group" preferably include a C$_{6-14}$ arylalkyl group (e.g., a benzyl group, a phenylethyl group, a diphenylmethyl group, a 1-naphthylmethyl group, a 2-naphthylmethyl group, a 2,2-diphenylethyl group, a 3-phenylpropyl group, a 4-phenylbutyl group, a 5-phenylpentyl group, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" group mean a group consisting of a sulphur atom bonded to an alkyl-, alkenyl- or alkynyl-group, which is bonded via the sulphur atom to the entity to which the group is bonded.

In accordance with an embodiment, the present invention provides compounds of formula II:

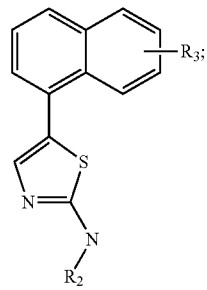

(II)

wherein R$_2$ is aryl or pyrimidyl group which may be substituted at C$_2$-C$_4$ with one or more C$_1$-C$_6$ alkyl groups or a halogen, and R$_3$ is one or more C$_1$-C$_6$ alkyl or substituted C$_1$-C$_6$ alkyl groups.

In accordance with an embodiment, the present invention provides a compound of formula III:

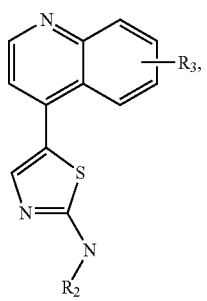

(III)

wherein R$_2$ is aryl or pyrimidyl group which may be substituted at C$_2$-C$_4$ with one or more C$_1$-C$_6$ alkyl groups or a halogen, and R$_3$ is one or more C$_1$-C$_6$ alkyl or substituted C$_1$-C$_6$ alkyl groups.

In accordance with an embodiment, the present invention provides a compound of formula IV:

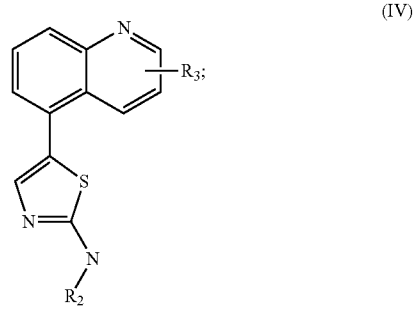

(IV)

wherein R$_2$ is aryl or pyrimidyl group which may be substituted at C$_2$-C$_4$ with one or more C$_1$-C$_6$ alkyl groups or a halogen, and R$_3$ is one or more C$_1$-C$_6$ alkyl or substituted C$_1$-C$_6$ alkyl groups.

In accordance with another embodiment, the present invention provides compounds of formula I, wherein the compound is selected from the group consisting of:

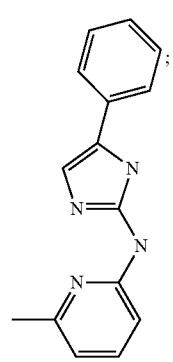

(1)

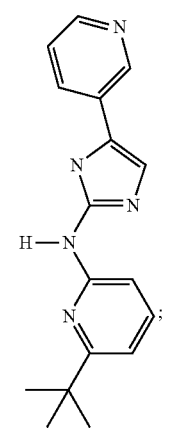

(2)

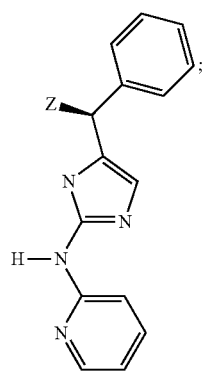
(3)
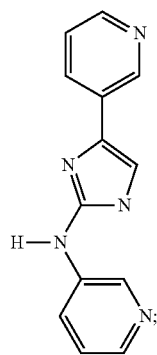
(4)
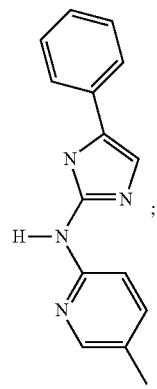
(5)
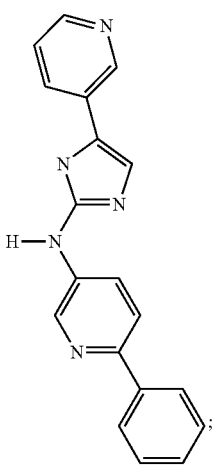
(6)
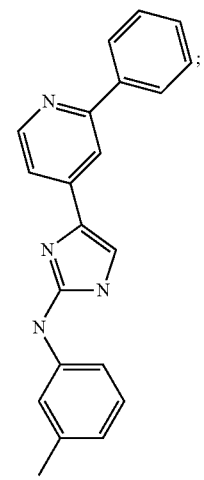
(7)
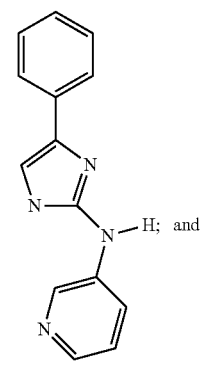
(8)
(9)

-continued

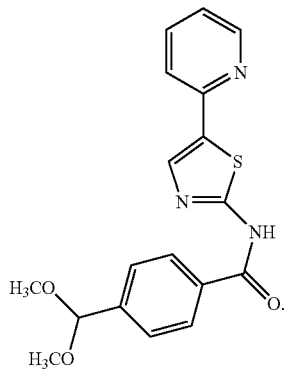

(10)

In accordance with an embodiment, the present invention provides a pharmaceutical composition comprising the compounds of formula I-IV, or a salt, solvate, stereoisomer, or prodrug thereof, and a pharmaceutically acceptable carrier.

Included within the compounds of the present invention are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In accordance with another embodiment, the present invention provides a pharmaceutical composition as described above, for use in a medicament, preferably for use in a medicament for the treatment of cancer or a proliferative disease in a subject comprising administering to the subject an effective amount of the medicament.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

Thus, in accordance with an embodiment, the present invention provides the compounds of formulas I-IV, or a pharmaceutical composition comprising the compounds of formulas I-IV, as described herein, as an inhibitor of LC3-Atg3 interaction in a subject.

In accordance with another embodiment, the present invention provides the compounds of formulas I-IV, or a pharmaceutical composition comprising the compounds of formulas I-IV, as described herein, as an inhibitor of hLC3-hAtg3 interaction in a subject.

In accordance with a further embodiment, the present invention provides the compounds of formulas I-IV, or a pharmaceutical composition comprising the compounds of formulas I-IV, as described herein, and at least one chemotherapeutic agent for treating a hyperproliferative disease or cancer in a subject.

Embodiments of the invention include a process for preparing pharmaceutical products comprising the compounds, salts, solvates or stereoisomers thereof. The term "pharmaceutical product" means a composition suitable for pharmaceutical use (pharmaceutical composition), as defined herein.

As used herein, the term "treat," as well as words stemming therefrom, includes preventative as well as disorder remitative treatment. The terms "reduce", "suppress" and "inhibit," as well as words stemming therefrom, have their commonly understood meaning of lessening or decreasing. These words do not necessarily imply 100% or complete treatment, reduction, suppression, or inhibition.

As used herein, the term "subject" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), and one which has little or no detrimental side effects or toxicity under the conditions of use. Examples of the pharmaceutically acceptable carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds of the present invention, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-$\beta$-aminopropionates, and 2-alkyl-imidazoline quaternary ammonium salts, and (e) mixtures thereof.

The parenteral formulations will typically contain from about 0.5% to about 25% by weight of the compound of the present invention or a salt, solvate or stereoisomer thereof, in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compound of the present invention, or a salt, solvate or stereoisomer thereof, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds of formulas I-IV of the present invention, or a salt, solvate or stereoisomer thereof, also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 100 mg/kg body weight of the subject being treated/day, preferably about 1 mg/kg/day to about 50 mg/kg/day. In some embodiments, the dosage levels of the compounds would be in the range of 10 µM to about 500 µM, preferably about 100 µM to about 300 µM.

Alternatively, the compounds of formulas I-IV of the present invention, or a salt, solvate or stereoisomer thereof, can be modified into a depot form, such that the manner in which the compound is released into the body to which it is administered is controlled with respect to time and location within the body (see, for example, U.S. Pat. No. 4,450,150). Depot forms of compound can be, for example, an implantable composition comprising the compound and a porous or non-porous material, such as a polymer, wherein compound is encapsulated by or diffused throughout the material and/or degradation of the non-porous material. The depot is then implanted into the desired location within the body and the compounds are released from the implant at a predetermined rate.

In one embodiment, the compounds of formulas I-IV of the present invention, or salts, solvates or stereoisomers thereof, provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the compounds of formulas I-IV is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds of the present invention, or salts, solvates or stereoisomers thereof, may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently, or in lower doses than with the unmodified compound.

It will be understood by those of ordinary skill in the art that the compounds described above can act as a "chemosensitizing" agent, allowing cancer cells or tumor cells to become more susceptible to the actions of one or more other chemotherapeutic agents, thereby increasing the chemotherapeutic effect and/or allowing a lower dosage of the chemotherapeutic agents to have a therapeutic effect on the tumor or cancer cells.

As used herein, the term "proliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis.

In accordance with one or more embodiments, the term "cancer" can include any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, cancers of the brain, including, for example, gliomas and neuroblastomas, ureter cancer, and urinary bladder cancer.

In an embodiment, the term "administering" means that the compounds of the present invention are introduced into a subject, preferably a subject receiving treatment for a proliferative disease, and the compounds are allowed to come in contact with the one or more disease related cells or population of cells in vivo.

It will be understood by those of ordinary skill in the art that the term "tumor cell" as used herein means a neoplastic growth which may, or may not be malignant. Additionally, the compositions and methods provided herein are not only useful in the treatment of tumors, but in their micrometastses and their macrometastses. Typically, micrometastasis is a form of metastasis (the spread of a cancer from its original location to other sites in the body) in which the newly formed tumors are identified only by histologic examination;

micrometastases are detectable by neither physical exam nor imaging techniques. In contrast, macrometastses are usually large secondary tumors.

In accordance with an embodiment, the present invention provides compositions and methods for the prevention and/or treatment of tumors, and their micrometastses and their macrometastses.

The term "therapeutic agent" or "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a proliferative disease. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

EXAMPLES

To be functional in autophagy processes, hLC3 undergoes two critical activation processes. First a C-terminal glycine has to be exposed through proteolytic cleavage by the serine protease Atg4. Second, a lipid, phosphatidylethanolamine (PE), is conjugated to the C-terminal glycine residue resulting in hLC3-PE (hLC3-II). The inventors previously discovered 4-formyl-N-(4-pyridin-2-yl-1,3-thiazol-2-yl)benzamide (PTA) as an autophagy inhibitor in their studies on the plasmodial system in search of protein-protein interaction inhibitors of the PfAtg8-PfAtg3 interaction, the homologous system in the malaria parasite. The lipidated form of either Atg8 or hLC3 (hLC3-II) can be resolved from the unlipidated form (hLC3-I) using SDS-PAGE due to their different migration speeds. Specific commercial antibodies for hLC3 detection were used in these studies to quantify the two species via Western blot in treated and untreated cancer cell lines.

MCF-7 cells were maintained in RPMI media supplemented with 10% fetal bovine serum. HepG2 cells were maintained in Dulbecco's modified Eagle medium (DMEM, Invitrogen) media supplemented with 10% fetal bovine serum and 1×MEM non-essential amino acids. For cytotoxicity experiments, cells were plated on T-75 flasks and grown until they reached at 70-80% confluency.

Cell proliferation was monitored in real-time cell electronic sensing (xCELLigence System, Acea Biosciences) through gold microelectrode arrays on the bottom of 96 E-Plates. 100 μl of corresponding culture media was added into each well of 96 E-Plates, which inserted into the station and background measurement was taken. Then, cells (5,000 cells/well in 100 μl) were seeded into 96 E-Plates containing 100 μl medium/well. After about 20 hours, 200 μl medium was discarded and replaced with 100 μl of fresh medium containing indicated amounts of compounds for each well. In the xCELLigence System the changes in cell number are detected as modifications in the measurement of electrical impedance and are represented as Cell Index (CI).

Example 1

Computational docking studies.

Figure 2A:
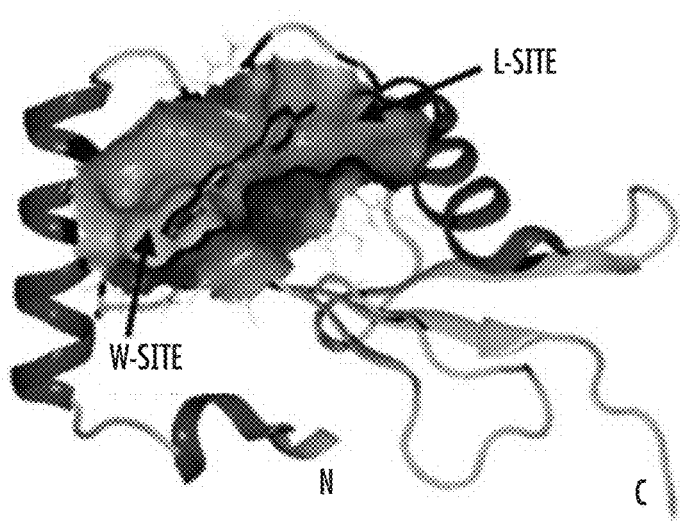
FIGS. 2A-2C depict the properties of the PTA-binding site on hLC3. 2A) Energy-minimized docking pose of PTA to hLC3. The pyridinylthiazolamine ringsystem predominantly binds to the W-site of hLC3. 2B) Conservation of amino acids between hLC3 and Plasmodium Atg8. Shown in yellow sticks is the bound peptide of Atg3. The W-Site is highly conserved, whereas the L-site is less conserved, explaining the lower affinity of hLC3 to PTA (FIGS. 2A, 2B adapted from Hain et al. 2013). 2C) Direct binding interaction of purified hLC3 or PfAtg8 to PTA immobilized on a SPR chip to determine their respective affinities.

Computational docking studies were performed to assess the binding site of PTA to hLC3 (FIG. 2A) using the OpenEye docking software FRED (OpenEye Scientific Software Inc., Santa Fe, N. Mex.). The highest scoring pose indicates binding of PTA predominantly to the W-/L-site. The L-site in the hLC3 crystal structure does not provide a deep groove as is the case in the Plasmodium structure described previously, but rather a more extended, flat hydrophobic patch.

Example 2

Surface Plasmon Resonance analysis.

Figure 2B:
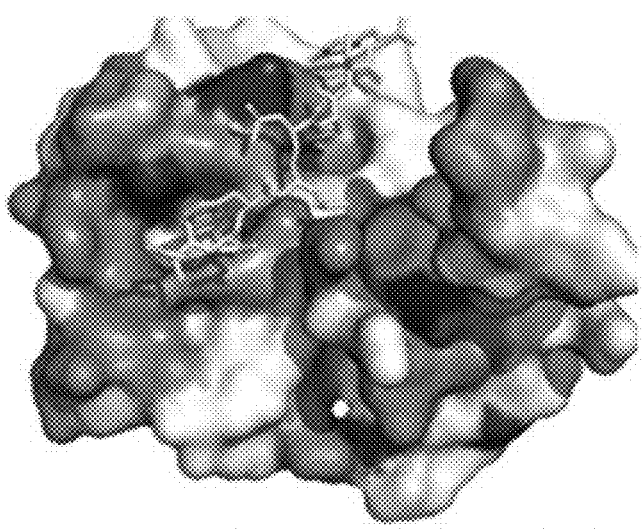
Figure 2C:
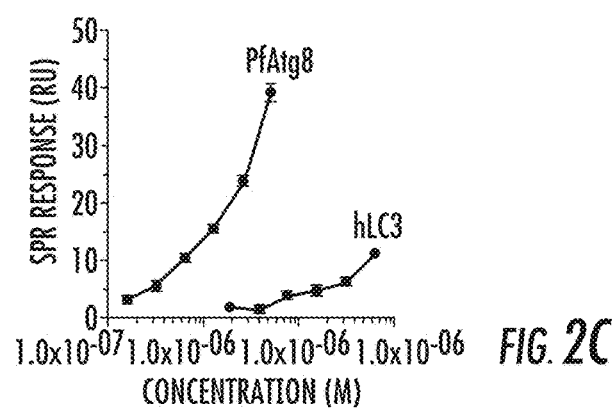

In comparing the sequence conservation of this W-/L-site between PfAtg8 and hLC3, it is apparent that the W-site has maintained a higher degree of conservation, as indicated by the magenta patch in FIG. 2B. To test whether or not the W-/L-site of Atg8 was indeed the interaction area to which our small molecules bind, we performed SPR binding studies with different Atg8-homologs, essentially mimicking mutational studies in the environment of the W-/L-site. This allowed us to explore the key features of the binding site in a manner that was much more efficient than introducing multiple single point mutations for each protein of interest at a time.

SPR studies were performed on PfAtg8 and hLC3 binding to the PTA molecule immobilized on an SPR chip. The results of these studies are consistent with observations about the mutations present in the respective W-/L-binding site (FIG. 3), confirming the computational docking studies and increasing the confidence in the proposed model for PTA binding. The color coding in FIG. 3 highlights divergent amino acid residues in red, which is well reflected in the decrease of binding affinity for hLC3 versus PfAtg8 to the immobilized PTA-molecule on the SPR chip.

Example 3

PTA-susceptibility screen of cancer cell lines.

Figure 4:
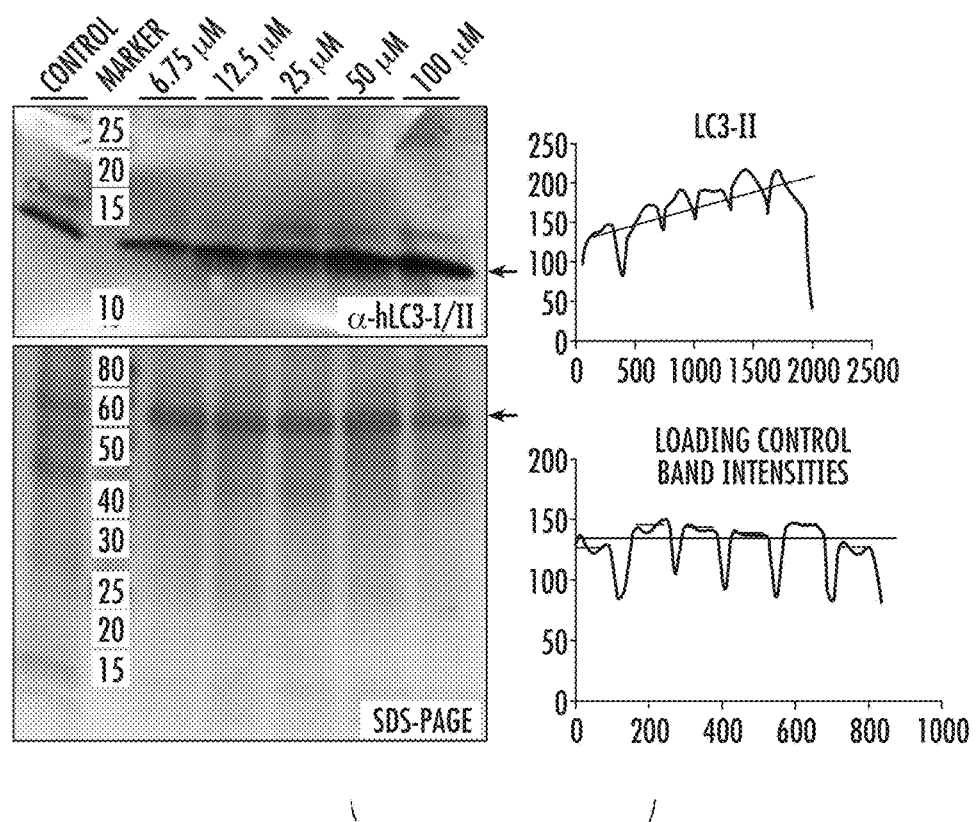
FIG. 4 provides an anti-LC3 Western blot of PTA treated HCT8 colon cancer cells with corresponding Coomassie stained 4-20% SDS-PAGE. The arrows indicate the band used for quantification with ImageJ. The SDS gel indicates approximate equal amounts were loaded per lane.

To show that PTA-molecules are able to bind to hLC3 in cell cultures, and prevent the lipidation of hLC3-I to hLC3-II, we exposed a human colon cancer cell line (HCT8) to PTA with concentrations ranging from about 100 μM to 6.25 μM. We used a DMSO-vehicle control. All experiments were carried out at 1% final DMSO concentration for 24 hours at 37° C. and 5% $CO_2$. Visual inspection by microscopy revealed attached and normal looking cells in the DMSO control only, and it revealed detached, blebbing cells with a concentration dependent phenotype in all of the treated samples. Only at the lowest concentration of 6.75 μM PTA were a few patches of attached cells still visible. The DMSO control sample was trypsinized to detach the cells from the culture dish. All cells were collected and spun down before resuspending them in SDS-loading dye for SDS-PAGE and Western blot analysis. Commercial monoclonal antibodies directed against hLC3 (D3U4C Rabbit mAB) and GAPDH (14C10 Rabbit mAB) as loading control were used. The Western blot clearly distinguishes between the un-lipidated (hLC3-I) and lipidated (hLC3-II) form by their migration speed in the SDS-gel (FIG. 4). The lipidated form migrates faster in an SDS-gel due to its additional negative charge from the conjugated phospholipid. An accumulation of the slower migrating hLC3-I band is visible, indicating that the PTA molecule of the present invention is capable of disrupting the lipidation stage in human cancer cell lines. A concentration of 30 µM PTA for 96 hours was well tolerated in HC-04 liver cells, without exhibiting a cytotoxic effect. The same assay will then be applied to our collection of cancer cell lines to assess which of the lines exhibit a similar decrease of the population of LC3-II and determine the respective $IC_{50}$ in a first-pass 6-point dose-dependent assay ranging from 20 µM to 80 µM. 0.5% DMSO will be used as a vehicle control and 33 nM Wortmannin as a positive control for autophagy inhibition.

Example 4

Our structural understanding of how the hLC3 binds the PTA-scaffold combined with surface plasmon resonance (SPR)-interaction studies, has enabled the inventors to design the PTA-analogs of the present invention with low $K_{off}$-rates. A low $K_{off}$-rate indicates that the ligand is bound to the target protein for a longer period of time as compared to a ligand with a fast $K_{off}$-rate. These new PTA-analogs are tested in SPR-based assays with purified recombinant hLC3 and hAtg3 to assess their ability to prevent the protein-protein interaction. Newly emerging molecules from our efforts are subjected to dose-dependent cell based screening with our cancer line collection.

Knowledge of the exact properties of the residues surrounding the binding pocket of hLC3 allows for the generation of specific, rationally designed probes that fit snugly into this pocket. The gold standard for this type of procedure is to generate these designs in correspondence with crystal structure, because the chemical properties and environment of the pocket can be defined and complemented by the results of mutagenesis and functional studies. Understanding the binding mode of the substrates Atg3 and Atg7 to hLC3 is important, since this knowledge will help to suggest properties that are likely to be required for small molecule probes to inhibit hLC3-PE conjugation at two different interfaces. Our co-crystal structure of the plasmodial PfAtg8 with PfAtg3 peptide has provided important insights, leading to the development of the first inhibitory molecules directly targeting this protein interaction.

About 120 PTA-homologs were identified in the PubChem database (pubchem.ncbi.nlm.nih.gov) that are available through commercial vendors. In a first assessment to determine which homologs to focus on initially, virtual library screening was performed with the known hLC3 structures (1UGM, 3ECI, 3WAL, 3WAO). Comparing the docking results from different structures of hLC3 allowed us to assemble a short list of nine high priority compounds (compounds 1-9). Further small molecules with the pyridinylthiazolamine (PTA) ring system will be identified, which demonstrate interaction with Atg8/LC3 and to improve the kinetic parameters of the small molecule binding with its target. Two complementary assays will be utilized, the first assesses the small molecule's ability to block the protein-protein interaction of hLC3 with hAtg3. The second assay is used to directly measure the binding of the small molecule to immobilized hLC3 on an SPR chip, which will allow us to draw conclusions about the physical interaction between the two binding partners.

Example 5

To define the range of metastasizing cancer cell lines susceptible to PTA derivatives of the present invention, we can use the HUVEC electrical-impedance assay. Invasive tumor cell lines are monitored through electric impedance measurements of human umbilical vein endothelial cells (HUVEC) monolayers in the presence of PTA derivatives. In this assay a monolayer of human umbilical vein endothelial cells (HUVEC) is exposed to invasive tumor cell lines in the presence and absence of PTA or PTA-derivatives. The invasion potential of the tumor cell is measured by the change in cell impedance as the HUVEC monolayer junctions are compromised by the invading tumor cells. Cells can be monitored over multiple days while the real-time impedance is recorded.

Since the number of cells that have been seeded is known, the CI is related to the quantitative measurement of the electrical impedance present in the well and it displays in plots the changes of cells that adhere to the conducting metals on the bottom of the wells. Therefore, CI values increase or decrease in parallel with cell growth due to the insulating properties of the cell membrane attached to the bottom of the well. The data was processed according to the "sigmoidal dose-response" (variable slope nonlinear regression curve fit for an inhibitor), from which the $IC_{50}$ was obtained. The software generated a standard error value for the data points based on the fitted sigmoidal curve and the variability of the points around that curve. As a curve type for cytotoxicity DRC (CI at a time point vs. concentration) was used.

Figure 5:
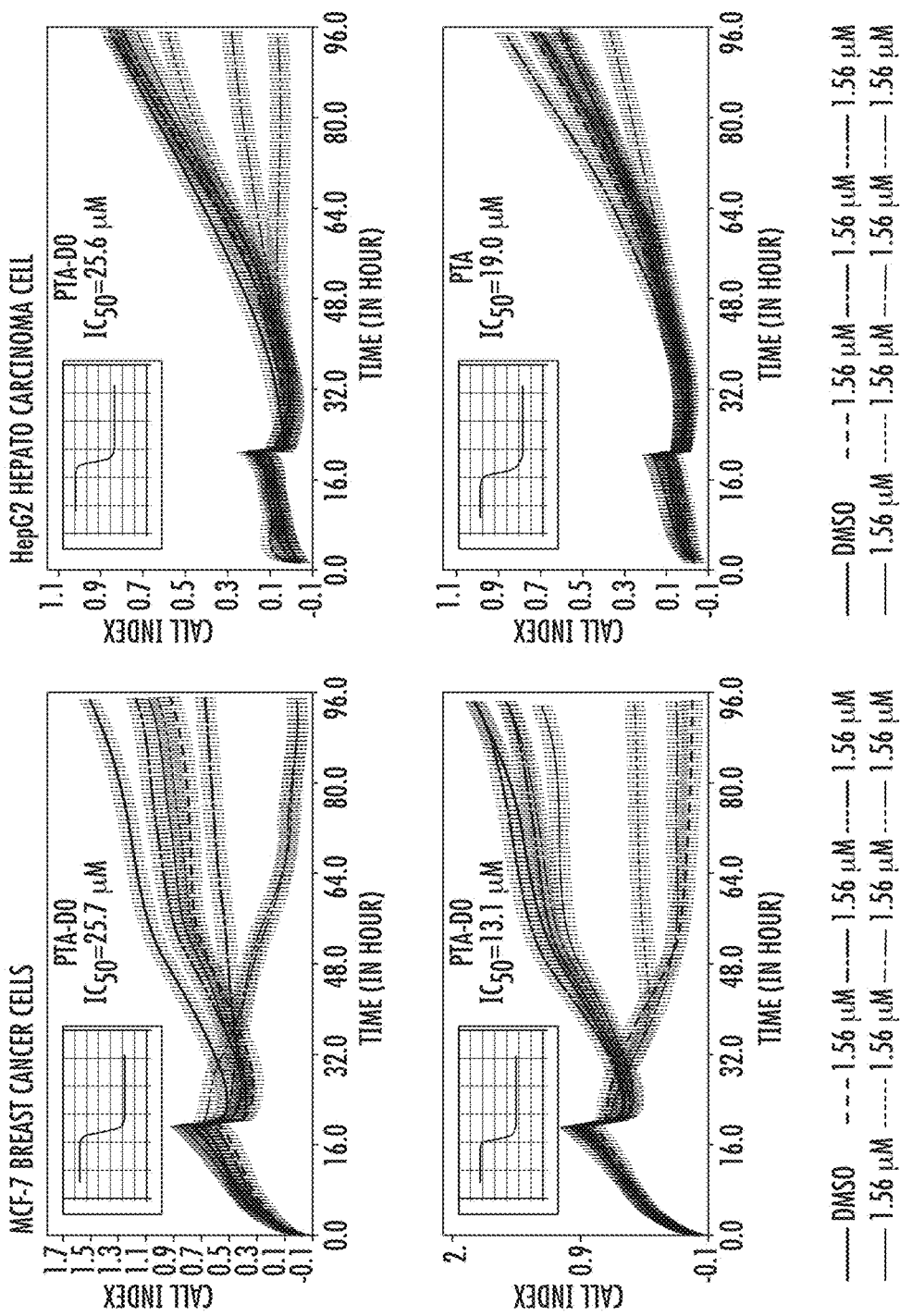
FIG. 5 depicts the concentration dependent effect of PTA and a synthesized derivative (Compound 10) on two cancer cell lines in a HUVEC impedance assay. PTA or Compound 10 were added ranging from 100 μM to 1.5 μM to the cells after 12 hours. The apparent $IC_{50}$ after 72 hours of drug treatment was calculated and is shown in the inset of each graph of the triplicate impedance measurement per concentration. The DMSO vehicle control is shown as dark red line. The observed $IC_{50}$ for PTA treatment in cells are in the same range as the affinity of hLC3 to PTA on the SPR chip of 18 μM.

Increased LC3-II levels are correlated with properties of metastasizing cancer cell lines. It is therefore thought that if LC3-II levels are reduced or inhibited, then the level of metastasizing cells should correspondingly decline. To test this hypothesis we have performed invasion assays with two cancer cell lines (MCF-7, a breast cancer cell line and HepG2, a hepatocarcinoma cell line), the results are shown in FIG. 5.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of formula I:

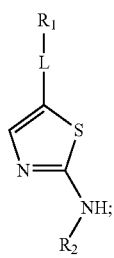

or salt solvate, or stereoisomer thereof, wherein $R_1$ is an pyrimidyl, napthalenyl or heteronapthalenyl group which may be substituted with one or more $C_1$-$C_6$ alkyl or substituted $C_1$-$C_6$ alkyl groups; wherein L is a linker group of 0 or 1, comprising an alkylamino group; wherein $R_2$ is aryl, pyrimidyl or pyrimidyl group wherein the pyridyl or pyrimidyl group is substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsulfonyl $C_1$-$C_6$ alkyl, hydroxyl $C_1$-$C_6$ alkyl, $C_1$-$C_6$ alkoxy, $C_1$-$C_6$ alkoxy $C_1$-$C_6$ alkyl, $C_3$-$C_8$ cycloalkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, and wherein the aryl group may be substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsufonyl $C_1$-$C_6$ alkyl, hydroxyl $C_1$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, or a halogen, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; and optionally wherein $R_2$ is linked to the aminothiazole ring of formula I by an amide linkage.

2. The compound of claim 1, having the formula:

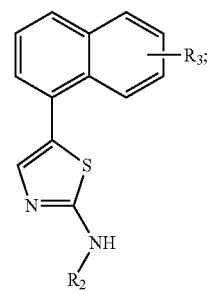

wherein $R_2$ is an aryl which may be substituted at $C_2$-$C_4$ with one or more $C_1$-$C_6$ alkyl groups or a halogen, or a or a pyrimidyl group which is substituted at $C_2$-$C_4$ with one or more $C_1$-$C_6$ alkyl groups or a halogen, and $R_3$ is a $C_1$-$C_6$ alkyl or substituted $C_1$-$C_6$ alkyl group.

3. The compound of claim 1, having the formula:

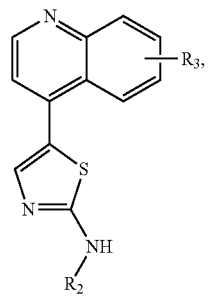

wherein $R_2$ is aryl which may be substituted at $C_2$-$C_4$ with one or more $C_1$-$C_6$ alkyl groups or a halogen, or a or a pyrimidyl group which is substituted at $C_2$-$C_4$ with one or more $C_1$-$C_6$ alkyl groups or a halogen, and $R_3$ is a $C_1$-$C_6$ alkyl or substituted $C_1$-$C_6$ alkyl group.

4. The compound of claim 1, having the formula:

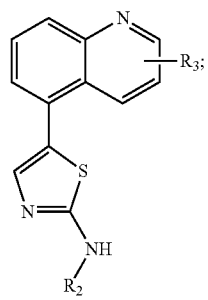

wherein $R_2$ is an aryl which may be substituted at $C_2$-$C_4$ with one or more $C_1$-$C_6$ alkyl groups or a halogen, or a or a pyrimidyl group which is substituted at $C_2$-$C_4$ with one or more $C_1$-$C_6$ alkyl groups or a halogen, and $R_3$ is a $C_1$-$C_6$ alkyl or substituted $C_1$-$C_6$ alkyl group.

5. A compound selected from the group consisting of:
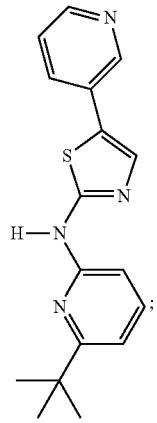
(2)
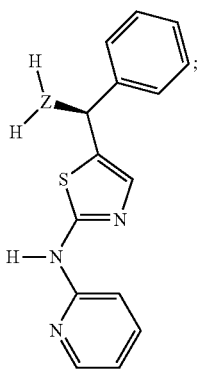
(3)
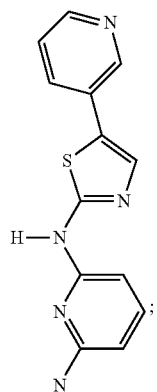
(4)
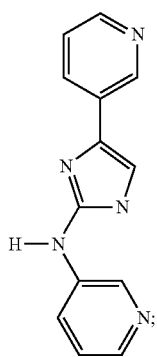
(5)
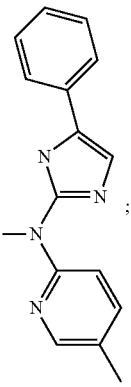
(6)
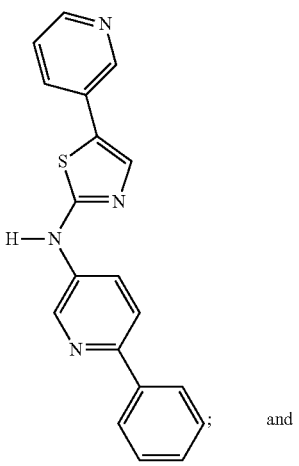
(7)
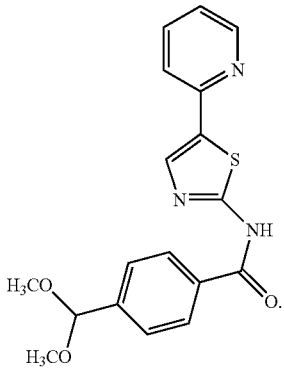
and
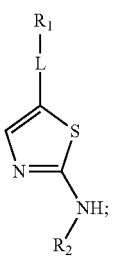
(10)
6. A pharmaceutical composition comprising one or more compounds of formula I:
(I)

or salt, or stereoisomer thereof, wherein $R_1$ is an, napthalenyl or heteronapthalenyl group which may be substituted with one or more $C_1$-$C_6$ alkyl or substituted $C_1$-$C_6$ alkyl groups; wherein L is a linker group of 0 or 1, comprising an alkylamino group; wherein $R_2$ is an aryl, pyridyl or pyrimidyl group wherein the pyridyl or pyrimidyl group is substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsulfonyl $C_1$-$C_6$ alkyl, hydroxyl $C_1$-$C_6$ alkyl, $C_1$-$C_6$ alkoxy, $C_1$-$C_6$ alkoxy $C_1$-$C_6$ alkyl, $C_3$-$C_8$ cycloalkyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, and wherein the aryl group may be substituted at $C_2$-$C_4$ with one or more $C_1$-$C_6$ alkylamino $C_1$-$C_6$ alkyl, $C_1$-$C_6$ dialkylamino $C_1$-$C_6$ alkyl, $C_1$-$C_6$ alkylamino $C_1$-$C_6$ alkyl, $C_1$-$C_6$ alkylthio $C_1$-$C_6$ alkyl, $C_6$-$C_{14}$ arylthio, $C_1$-$C_6$ alkylsulfonyl $C_1$-$C_6$ alkyl, hydroxyl $C_1$-$C_6$ alkyl, $C_1$-$C_6$ alkoxy, $C_1$-$C_6$ alkoxy $C_1$-$C_6$ alkyl, $C_3$-$C_8$ cycloalkyl, heterocyclyl, $C_1$-$C_6$ alkylamino, di $C_1$-$C_6$ alkylamino, $C_1$-$C_6$ alkylthio, $C_2$-$C_6$ alkenylthio, $C_2$-$C_6$ alkynylthio, $C_6$-$C_{14}$ aryloxy, $C_2$-$C_6$ acyloxy, thio $C_2$-$C_6$ acyl, amido, and sulphonamido, and $C_1$-$C_6$ alkyl, and $C_2$-$C_6$ alkenyl, $C_2$-$C_6$ alkynyl, or a halogen, wherein each of alkyl, aryl, or heterocyclyl moiety may be unsubstituted or substituted with one or more substituents selected from the group consisting of halo, hydroxyl, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidine, aldehyde, ureido, and aminocarbonyl; and optionally wherein $R_2$ is linked to the aminothiazole ring of formula I by an amide linkage, and a pharmaceutically acceptable carrier.

7. A pharmaceutical composition selected from the group consisting of:

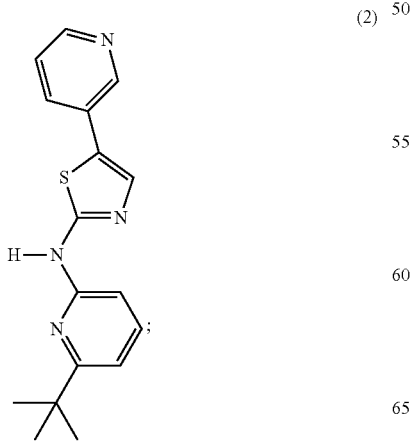

(2)

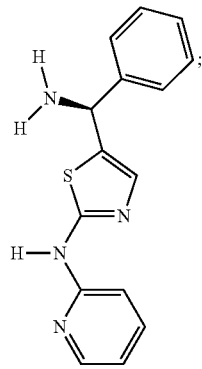

(3)

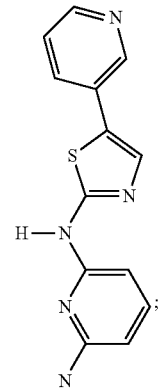

(4)

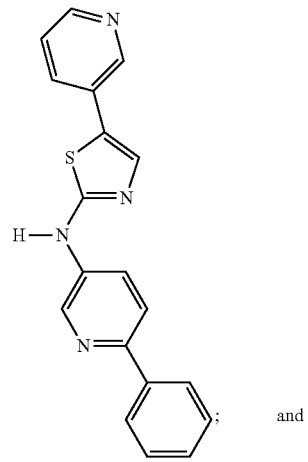

(7)

; and

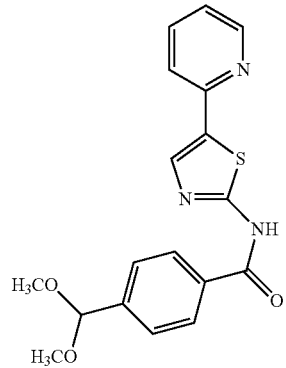

(10)

and a pharmaceutically acceptable carrier.

8. The pharmaceutical composition of claim 6, wherein the composition further comprises at least one chemotherapeutic agent.

9. The pharmaceutical composition of claim 8, wherein the chemotherapeutic agents are selected from the group consisting of alkylating agents, angiogenesis inhibitors, aromatase inhibitors, antimetabolites, anthracyclines, antitumor antibiotics, monoclonal antibodies, platinums, topoisomerase inhibitors, and plant alkaloids.

10. The pharmaceutical composition of claim 7, wherein the composition further comprises at least one chemotherapeutic agent.

11. The pharmaceutical composition of claim 10, wherein the chemotherapeutic agents are selected from the group consisting of alkylating agents, angiogenesis inhibitors, aromatase inhibitors, antimetabolites, anthracyclines, antitumor antibiotics, monoclonal antibodies, platinums, topoisomerase inhibitors, and plant alkaloids.

* * * * *